United States Patent [19]
Sepetka et al.

[11] Patent Number: 6,001,111
[45] Date of Patent: Dec. 14, 1999

[54] LOW PROFILE VESSEL OCCLUDER WITH AND WITHOUT DETACHABLE APPLICATOR

[75] Inventors: Ivan Sepetka, Los Altos, Calif.; Robert G. Matheny, Carmel, Ind.; James A. Magovern, Pittsburgh, Pa.; Dwight P. Morejohn, Davis; Robert C. Glines, Cameron Park, both of Calif.

[73] Assignee: Cardiothoracic Systems, Inc., Cupertino, Calif.

[21] Appl. No.: 09/008,113

[22] Filed: Jan. 16, 1998

[51] Int. Cl.⁶ ..................................................... A61B 17/00
[52] U.S. Cl. .............................................................. 606/158
[58] Field of Search ..................................... 606/157, 158, 606/159, 151, 232, 139, 148, 203

[56] References Cited

U.S. PATENT DOCUMENTS

| | | | |
|---|---|---|---|
| 3,123,077 | 3/1964 | Alcamo | 606/228 |
| 3,845,760 | 11/1974 | Birman | 606/203 |
| 3,880,166 | 4/1975 | Fogarty | 606/158 |
| 3,910,281 | 10/1975 | Kletschka et al. | 606/158 |
| 4,177,813 | 12/1979 | Miller et al. | 606/158 |
| 4,988,355 | 1/1991 | Leveen et al. | 606/158 |
| 5,441,509 | 8/1995 | Vidal et al. | 606/151 |
| 5,626,590 | 5/1997 | Wilk | 606/148 |
| 5,861,003 | 1/1999 | Latson et al. | 606/213 |

*Primary Examiner*—Michael Buiz
*Assistant Examiner*—Vikki Trinh
*Attorney, Agent, or Firm*—Lyon & Lyon LLP

[57] ABSTRACT

A low profile unobtrusive occluder device is disclosed which is particularly applicable for occluding blood vessels in minimally invasive beating heart CABG surgical procedures, wherein relatively small surgical openings are provided. At least one flexible member is provided on the occluder, which is placed against the vessel. A suture thread is passed under the vessel to encompass the vessel between the occluder and suture thread. The suture thread is selectively attached to the occluder such that the flexible member, when deformed, applies continuous selected tension on the suture thread to apply a corresponding compression on the vessel which occludes the flow of blood. An applicator is attached to the occluder to enable installation thereof, but is detachable after installation such that only the low profile occluder remains on the heart surface during surgery. The applicator is re-attached to the occluder to facilitate removal of the latter. In an alternative embodiment, the occluder is formed as an adjustable part of a heart contacting member of a thoracotomy stabilizer apparatus.

26 Claims, 6 Drawing Sheets

LOW PROFILE VESSEL OCCLUDER WITH AND WITHOUT DETACHABLE APPLICATOR

FIELD OF THE INVENTION

The present invention relates generally to instruments utilized in cardiopulmonary bypass (CPB) surgical procedures and more particularly, to an occluder device for engaging an artery or the like to substantially reduce or eliminate the flow of blood through the artery.

BACKGROUND OF THE INVENTION

Diseases of the cardiovascular system affect millions of people each year. A particularly prevalent form of cardiovascular disease is a reduction in the blood supply leading to the heart caused by atherosclerosis or other conditions that create a restriction in blood flow at a critical point in the cardiovascular system that supplies blood to the heart. In many cases, such a blockage or restriction in the blood flow leading to the heart is treated by a surgical procedure known as a Coronary Artery Bypass Graft (CABG) procedure, which is more commonly known as a "heart bypass" operation. In the CABG procedure, the surgeon "bypasses" the obstruction in, for example, a target coronary artery to restore normal blood flow to the heart by attaching an available source vessel to the obstructed coronary artery or by removing a portion of a vein or artery from another part of the body to use as a graft, and by installing the graft at points between the source vessel and the target artery to restore normal blood flow.

Although the CABG procedure has become common, the procedure itself is lengthy and traumatic and can damage the heart, the cardiovascular system, the central nervous system, and the blood supply itself. In a conventional CABG procedure, the surgeon must cut through the entire length of the sternum (a sternotomy), perform several other procedures necessary to attach the patient to a heart-lung bypass machine, clamp the aorta to stop the blood flow to the coronary arteries and infuse cardioplegia to stop the heart from beating in order to complete the bypass grafts.

In recent years, surgeons have begun performing CABG procedures using surgical techniques especially developed so that the CABG procedure can be performed while the heart is still beating. In such procedures, there is no need for any form of cardiopulmonary bypass, no need to perform the extensive surgical procedures necessary to connect the patient to a cardiopulmonary bypass machine, and no need to stop the heart. As a result, the "beating heart" surgery is much less invasive and the entire procedure can typically be achieved through a small number, typically one or two, comparatively small incisions in the chest.

As noted above, the CABG procedure requires that a fluid connection for restoring the flow of blood be established between two points to "bypass" a diseased or obstructed area to restore blood flow to the heart. Typically, a source vessel, such as a source artery with an unobstructed blood flow, for example, the left internal mammary artery (LIMA), or a bypass-graft having one end sewn to an unobstructed blood source such as the aorta, is anatomosed or sewn to a target occluded coronary artery, such as the left anterior descending (LAD) artery or other vessel, that provides blood flow to the muscles of the heart. Because the beating-heart CABG procedure is performed while the heart muscle is continuing to contract and pump blood, the anastomosis procedure is difficult to perform because the heart continues to move while the surgeons is sewing the anastomosis. However, it is important that the anastomosis be performed as rapidly as possible because the blood flow through the target coronary artery may be temporarily interrupted or reduced to avoid excessive blood loss. Also, the working space and visual access are limited because the surgeon may be working through a small incision in the chest or may be viewing the procedure on a video monitor if the site of the surgery is viewed via a surgical scope.

Accordingly, it is highly desirable to provide a surgeon with surgical instruments and techniques which allow either the sternotomy, or particularly the beating heart surgery, to be performed more rapidly and with as little trauma as possible to the patient. In addition, it is advantageous to provide the surgeon with compact surgical instruments, particularly in minimally invasive surgical procedures such as the beating heart procedures of previous mention, where the space within a surgical opening is very restricted. In a median sternotomy procedure where the chest is opened and a relatively large surgical opening is provided, the need for compact instruments may not be critical. However, compact surgical instruments which also enhance the efficiency of a surgical procedure, while improving upon the space which is available to a surgeon for viewing the surgical site as well as for accommodating the surgeon's hands, are advantageous and of value to the surgeon.

In a surgical procedure for constructing an anastomosis in which the LIMA is sewn to the LAD, it is necessary to pinch-off, or occlude, the LAD proximal to the anastomosic site to substantially reduce or eliminate the flow of blood therein. Typically, a surgeon occludes the artery by threading a silastic suture around the artery once or twice and tightening the suture in selected manner to compress and thus choke the artery until the flow of blood ceases. In another technique and associated occluder device for occluding an artery, a silastic suture is threaded through a choker tube, around the artery and back through the tube. A surgeon occludes the artery by gently pulling on the ends of the suture while pushing the choker tube towards the artery until blood flow ceases, and then clamping the tube walls against the suture via forceps, for example, to secure the occluder device in place. In these procedures, it is difficult to control the degree of tightness when applying the suture, which may result in trauma to the LAD. Further, the silastic suture, once secured, is only capable of applying a continuous preselected compression to the vessel. In addition, it is difficult to remove the tightened silastic suture which generally is embedded in the epicardium as well as in the surrounding tissue.

Other occluder configurations presently are available wherein the occluder is attached to, and thus is an adjunct part of, a stabilizer apparatus which is employed, for example, in a beating heart surgical procedure to maintain the surgical opening, that is, the thoracotomy. Examples of the stabilizer and occluder combination, as well as of such stabilizers alone, are disclosed in a copending U.S. patent application Ser. No. 08/603,758 filed on Feb. 20, 1996 and U.S. patent application Ser. No. 08/789,751 filed on Jan. 27, 1997, both entitled Surgical Instruments and Procedures for Stabilizing the Beating Heart During Coronary Artery Bypass Graft Surgery, which are incorporated herein by reference.

SUMMARY OF THE INVENTION

The present invention provides an occluder surgical instrument which overcomes the various disadvantages of the typical occluders of previous mention. The invention is particularly applicable in the minimally invasive, beating heart surgical procedures, wherein low profile compact surgical instruments are highly desirable to enhance visualization and manipulation of the instruments through the relatively small surgical openings and at the level of the heart surface where room for doing the anastomosis is critical. In addition, the invention provides an occluder which is easily and quickly installed via an applicator which is then detached, thereby presenting a device with the desirable unobtrusive low profile during the surgery. After surgery, the same applicator is quickly reattached to the occluder which then is readily removed.

To this end, several embodiments of the occluder and of the applicator for installing the occluder, are contemplated by the present invention. To illustrate, the occluder generally includes an artery contacting central portion which terminates at either side in flexible "wings" of a thickness generally less than the thickness of the central portion. A suture preferably is attached to one wing of the occluder. The opposite wing is provided with a slit, notch, etc., herein termed a "v-lock", of a dimension and configuration which wedges or otherwise traps the free end of the suture therein. The central portion includes a bore therein of a selected configuration which, in the example herein, is internally threaded. An applicator, comprising a handle formed of an elongate rod, is threaded at its distal end to match the internally threaded bore in the central portion of the occluder, whereby the handle may be detachably attached to the occluder.

In an alternative embodiment, the applicator handle is hollow to include a lumen, and a rod with the distal threaded end is rotatably and translatably supported within the lumen of the handle. The distal end of the hollow handle includes a grip, or holder, which holds the occluder to prevent rotation thereof relative to an artery when the rod is being threaded to, or unthreaded from, the occluder.

In installation, the free end of the suture is passed under the selected artery and is pulled through until the occluder is pulled down into contact with the artery. The suture then is slipped into the slit or notch, that is, the v-lock, in the wing of the occluder and, while the occluder is held in place against the artery by means of the handle, the suture is pulled to cause the wings to bend and apply tension to the suture to provide the desired occlusion of the artery. The extra length of the suture is clipped off and the handle is unthreaded from the occluder, thereby leaving only the low profile occluder in place on the heart surface at the surgical site.

The occluder is removed by first threading the handle back into the occluder's threaded bore and then pulling the end of the suture away from the v-lock in the occluder wing via a pair of forceps, or cutting the suture with scissors. Then the handle and occluder are withdrawn from the site and the artery is restored.

Thus, an object and advantage of the present invention is to provide a low profile occluder which does not obstruct the view or activities of a surgeon.

Another object and advantage of the invention is to provide an occluder which continuously maintains a constant and selectable or calibrated tension against an artery to thus maintain a continuously firm yet atraumatic occlusion thereof.

It is a further object and advantage of the invention to provide a complementary applicator handle which is quickly attached to and detached from the low profile occluder to allow ready installation and removal of the occluder.

It is another object and advantage of the invention to provide an occluder of the invention in adjustable combination with a heart contacting member of a stabilizer apparatus.

These and other objects and advantages of the present invention will be more fully understood and appreciated by reference to the drawings and the following description of the invention.

DETAILED DESCRIPTION OF THE INVENTION

Various preferred and exemplary embodiments of the occluder and applicator of the present invention and of the method of installation thereof are described in various detail with reference to the figures. It is to be understood that similar reference numbers are used throughout the figures for like elements or components of the invention. For purposes of description, the present invention is described in the context of the application of occluders to an artery or vessel during a CABG surgical procedure. However, this specific application is intended for purposes of example only, and it is understood that those skilled in the relevant art will appreciate that the present invention has application in other surgical procedures.

Figure 1:
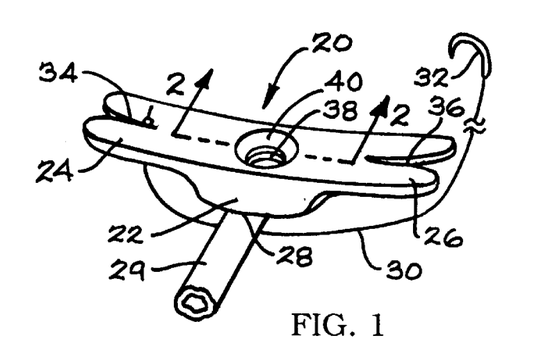
FIG. 1 is a perspective view illustrating an embodiment of an occluder in accordance with the present invention.

FIG. 1 illustrates an embodiment of the occluder 20 configuration of the invention, comprising basically a generally central main member 22 having a generally block-like structure, which has flexible members herein termed "wings" 24, 26, integrally formed with an upper portion at either end of a first and second end of the main member, respectively. Thus the lower portion of the generally block-like main member 22 extends downward a selected thickness to terminate at the bottom thereof in a surface 28 of selected contour, smoothness and composition for atraumatic engagement or contact with a vessel 29. Examples of several variations in the surface 28 are illustrated in FIGS. 3 and 4A–4E.

Figure 1A:
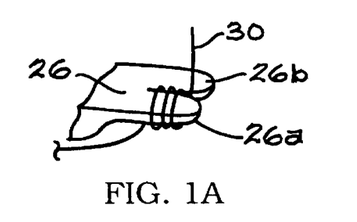
FIGS. 1A and 1B are perspective views illustrating an alternative method of securing a suture thread and an alternative embodiment of the suture-thread, respectively.

A suture thread 30 of predetermined length has a conventional surgical needle 32 attached to one end thereof, and is preferably permanently affixed at the other end to the wing 24. As depicted, the main body/wings configuration of the occluder may be symmetrical, with respective slits or notches, hereinafter referred to as "v-locks" 34, 36, formed generally midway in the ends of the wings 24, 26, whereby the end of the suture thread 30 may be permanently embedded in the v-lock 34 to prevent slipping of the respective end of the suture. The symmetry facilitates the fabrication process, however other configurations and manners of fastening the permanent end of the suture thread 30 to the occluder are apparent and intended, as further discussed below. The v-lock 36 in the wing 26 is configured to receive and lock therein the suture thread 30 after the latter is threaded via the needle 32 about the vessel 29. Exerting a force upward on the suture thread 30 compresses the vessel 29, bends the wing 24 down and wedges the respective end of the suture into the v-lock 36 to maintain the tension on the suture thread 30 via the bent wings 24, 26 to force the main member 22 to apply compression on the vessel 29. The suture may be wrapped several times about one of the half portions 26a or 26b of the wing 26, as depicted in FIG. 1A, to insure that the suture does not slip or loosen. The installation and removal procedures are described in full in FIGS. 7–12.

Figure 1B:
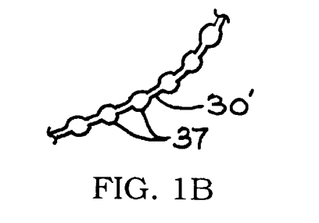

The suture thread 30 may be modified as depicted in FIG. 1B, to include pre-formed "knots" or "bumps" 37 along its length which insure that the suture thread does not slip from within the v-lock 36. The modified suture thread 30' and its manner of use are further described in the embodiments of FIGS. 14–16.

Figure 2A:
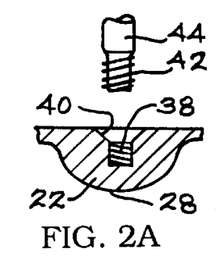
FIGS. 2A and 2B are partial cross-sectional views taken along section line 2—2 of FIG. 1, and including threaded tips of the applicator rod further depicted in FIGS. 6–16.
Figure 2B:
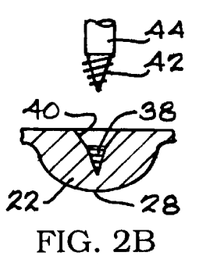

The main member 22 includes an internally threaded bore 38 centered therein which terminates at the top in a beveled truncated cone surface 40. As further depicted in FIGS. 2A, 2B, the cone surface 40 acts as a lead-in guide for an externally threaded tip 42 of a rod 44 which forms an applicator device for installing the occluder in accordance with the invention. Only the distal end of the rod 44 with the threaded tip 42 is shown in FIGS. 2A, 2B, but various embodiments of the applicator are fully described in the FIGS. 7–16. FIG. 2A illustrates a straight thread configuration for the applicator 44, while FIG. 2B illustrates a fast-locking tapered thread configuration which requires less rotation of the rod 44 to fully engage the matching threads 38.

Figure 3:
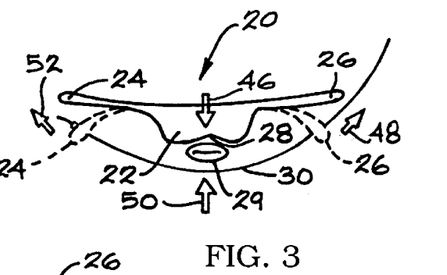
FIG. 3 is a side view illustrating an occluder of the invention before and after it is installed on a vessel.
Figure 4:
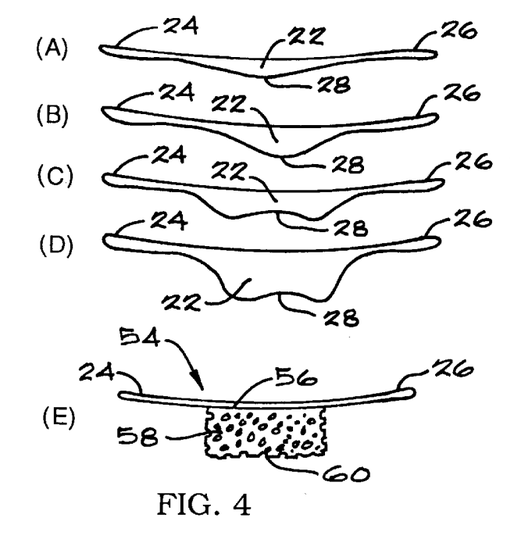
FIGS. 4A–4E are side views illustrating alternative configurations and compositions for the occluder of the present invention.

FIG. 3 diagramatically illustrates the configuration of the occluder 20 of FIG. 1 before and after it is installed on the vessel 29. To this end, the occluder 20 is shown in a relaxed state in solid line. During installation, a very slight force is applied on the main member 22 to lightly engage the vessel 29 with the surface 28. Simultaneously, as depicted in phantom line, the free end of the suture thread 30 is pulled through the v-lock 36 in the wing 26. Continued pulling upward on the suture thread 30 (arrow 48) bends the wings 24, 26 down while the suture is forced upward (arrow 50) to compress the vessel 29 between the suture 30 and the surface 28 of the main member 22, to substantially reduce or eliminate the flow of blood. After installation, the bowed wings 24, 26 exert relatively constant and continuous tension on the suture thread 30, as depicted by arrows 48 and 52, to maintain a resulting relatively constant and continuous compression of the vessel 29, as indicated by arrow 46. The amount of compression is selected in situ, that is, is selected at the moment of occlusion as a surgeon watches the blood flow decrease while applying tension on the suture thread 30. The occluder 20 then maintains the resulting suture tension.

FIGS. 4A–4E illustrate various different shapes which may be employed by the occluder of the invention. Thus, FIGS. 4A, 4B depict the main member 22 with different thicknesses, with both being less thick than the main member 22 of FIG. 1. In addition, the vessel engaging surfaces 28 of FIGS. 4A, 4B are generally convex in shape.

The main member 22 in FIG. 4C is generally the thickness of that of FIG. 2B, but the surface 28 of the occluder in FIG. 4C is generally concave in shape in the area thereof which engages the vessel 29. Likewise in FIG. 4D the vessel engaging surface 28 is generally concave in shape, but the main member 22 is thicker to thereby protrude further below the wings 24, 26. This configuration, as in FIGS. 1 or 3, allows the application of greater tension on the suture thread 30 and thus is capable of exerting greater compression on the vessel 29. In addition, the different configurations also accommodate different anatomical relationships regarding the location of the vessel relative to the myocardium and fatty tissue.

FIG. 4E illustrates an alternative embodiment 54 of the occluder formed of a flexible piece of material of a thickness similar to the thickness of the flexible wings 24, 26 of previous discussion. However, a main member 58 is formed of a piece of sponge or foam material bonded or glued to the central portion of the flexible piece of material and terminating at the bottom in a vessel-engaging surface 60. Thus, it may be seen that many different configurations and compositions are intended for the occluder within the scope of the present invention.

Figure 5:
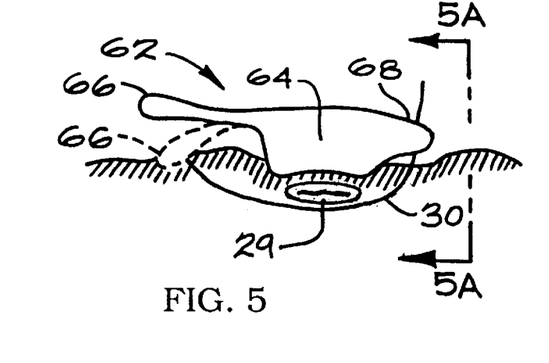
FIGS. 5 and 5A are side and end views, respectively, illustrating another alternative embodiment of the invention.
Figures 5A, 6:
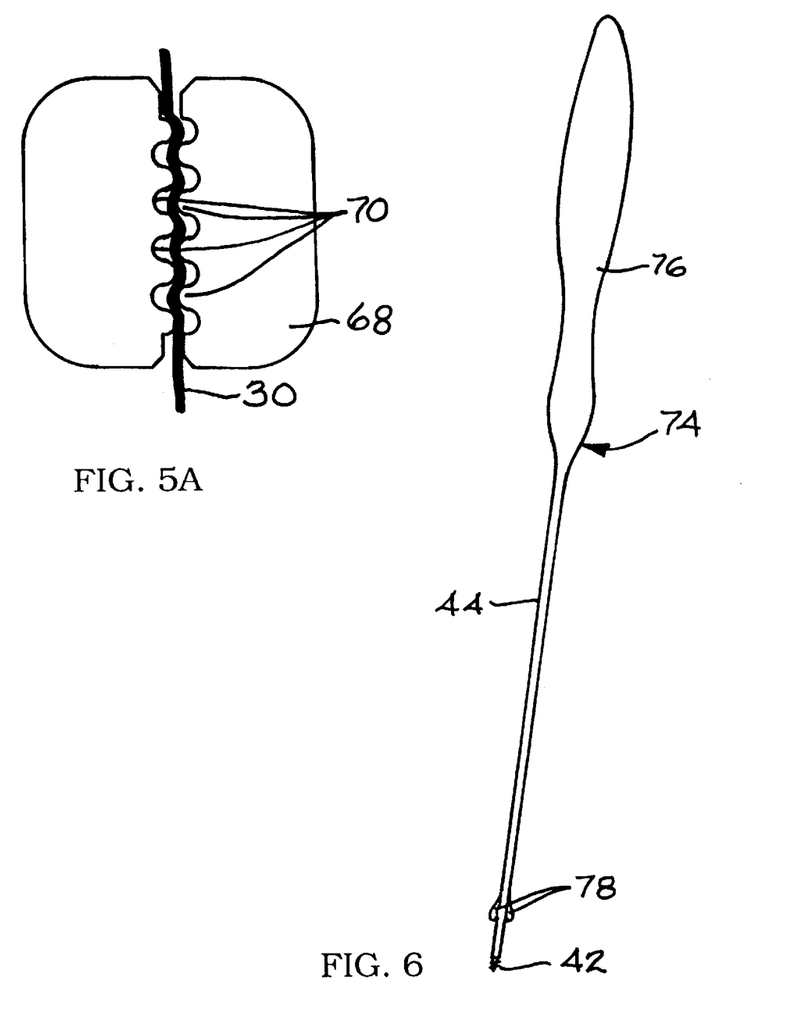
FIG. 6 is a perspective view illustrating an embodiment of an applicator of the present invention.

FIGS. 5 and 5A illustrate another alternative embodiment 62 of the invention wherein the occluder is not symmetrical in overall configuration. More particularly, a main member 64 similar to the main member 22 of FIGS. 1–4, has formed thereon a flexible wing 66 similar to the wing 24 of the previous figures. One end of the suture thread 30 is selectively secured to the end of the wing 66, also as previously described. However, in FIGS. 5, 5A the wing 26 of the previous figures is replaced with a blunt end member 68 integrally formed with the main member 64. As illustrated in FIG. 5A, the member 68 is vertically split and the confronting surfaces of the split have formed thereon alternating meshing ridges and grooves 70 extending generally horizontally in confronting relation. When the occluder 62 is being installed on the vessel 29 as described in FIG. 3, the suture thread 30 is pulled up against the vessel to bend the flexible wing 66 down (as depicted in phantom line). Then the suture thread 30 is pulled sideways into the ridges and grooves 70 to lock the thread in place. That is, the friction created by the confronting, alternate, meshed ridges and grooves 70 provides an alternative v-lock which allows sideways movement of the suture thread 30 but prevents movement of the thread vertically.

FIG. 6 illustrates an embodiment of an applicator 74 of previous mention in FIGS. 2A, 2B. In accordance with the invention, the applicator 74 includes the elongate thin rod 44 integrally formed with a generally flattened handle 76 for facilitating handling of the applicator by a surgeon. The rod 44 terminates at its distal end in the externally threaded tip 42 of, for example, FIGS. 2A or 2B. A pair of downward facing hooks 78 are formed at opposite sides of the rod 44 a short distance above the tip 42. A single hook 78 may be used, but opposite hooks are more convenient. The hooks 78 provide suture thread guides which facilitate the application of tension to the suture thread 30 during the installation procedure, as is fully described in FIGS. 7–10.

Figures 7, 8:
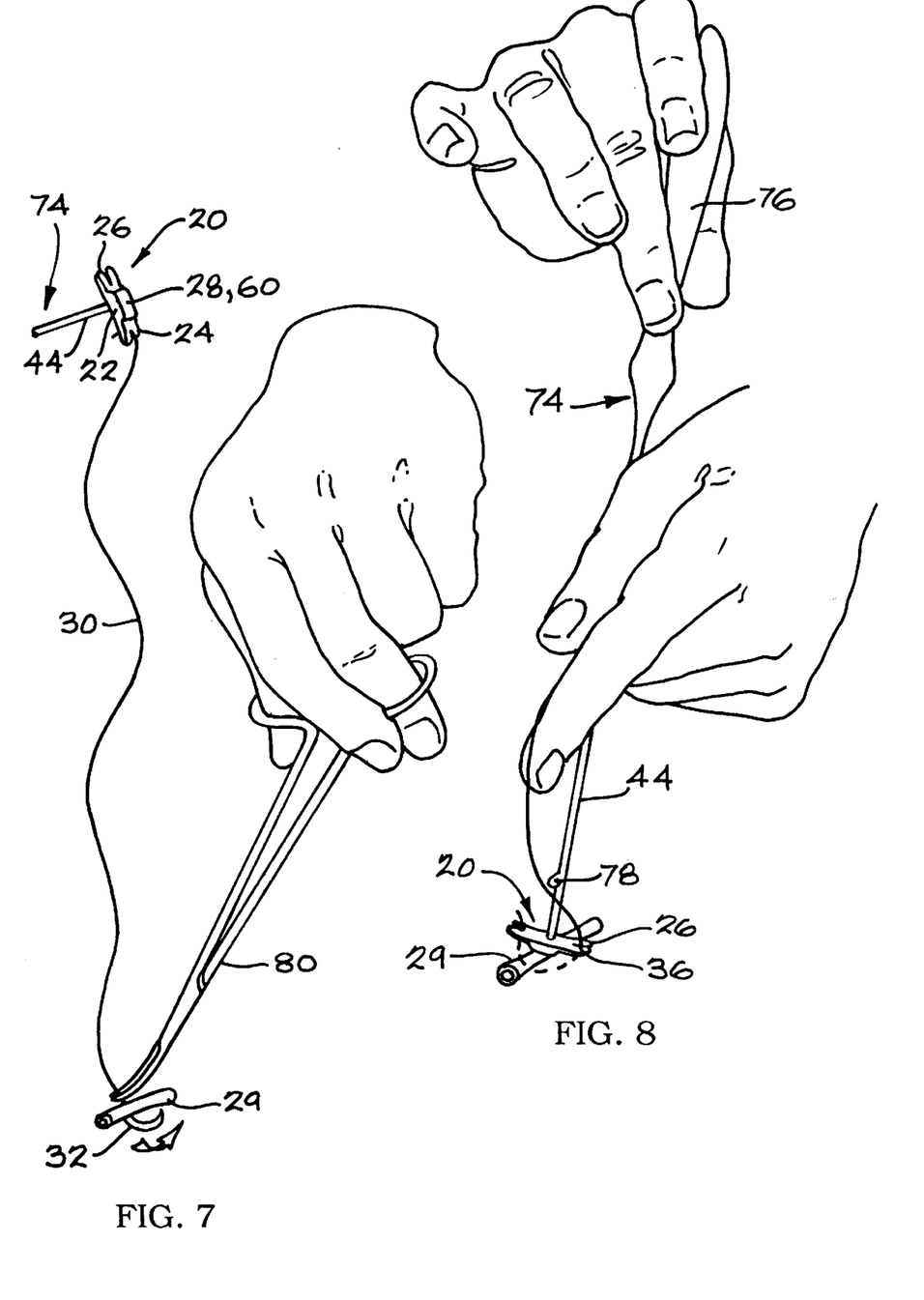
FIGS. 7–10 are perspective views illustrating several steps for installing an occluder on a vessel utilizing the applicator of FIG. 6, in accordance with the invention.
Figures 9, 10:
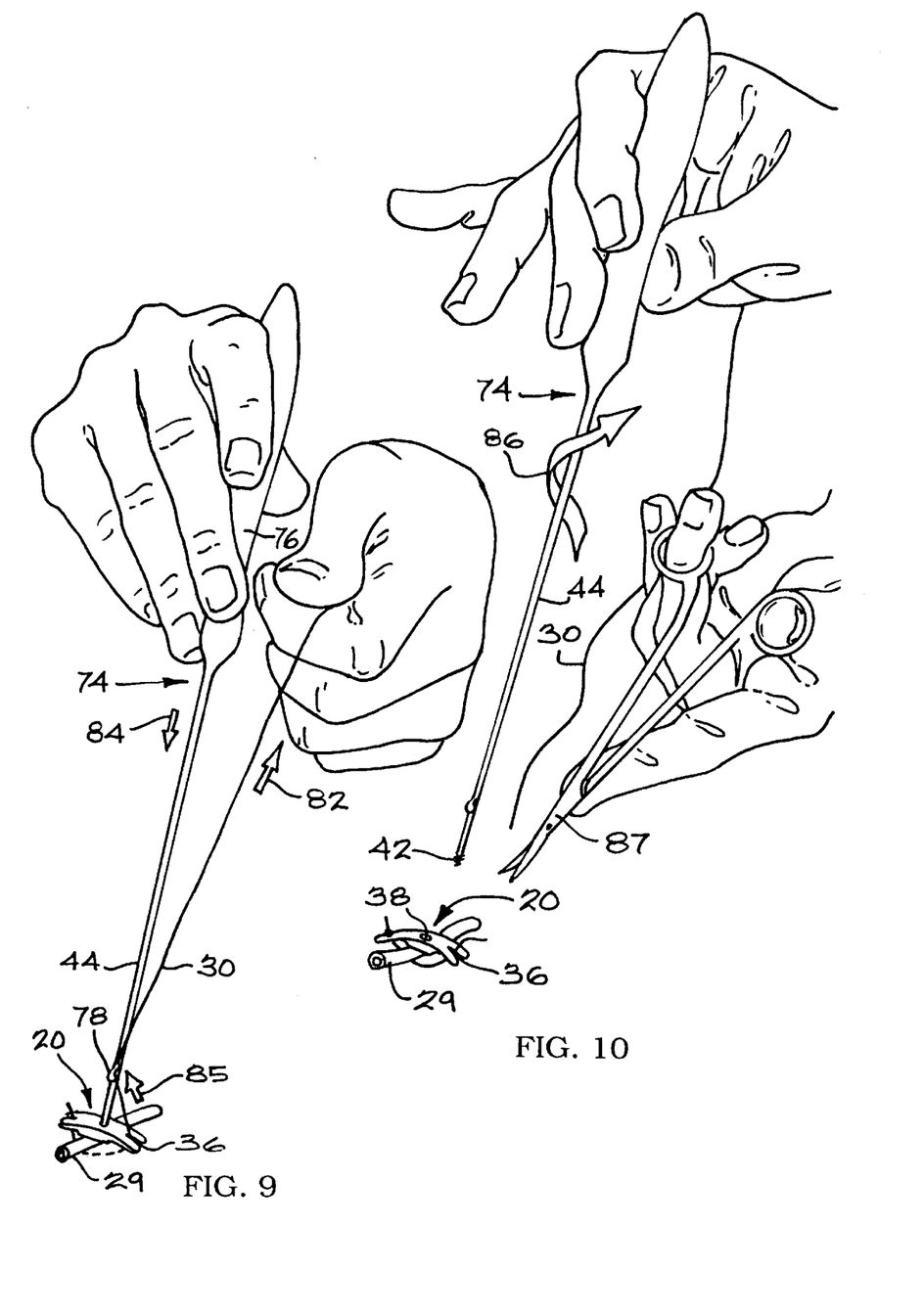

To this end, FIG. 7 illustrates the beginning of the occluder installation in accordance with the invention employing the occluder 20 (or 54, 62) threadably secured to the applicator 74 via the threaded bore 38 and tip 42 (FIGS. 2A, 2B). A surgeon takes a bite under the coronary vessel 29 with the needle 32 using conventional forceps/needle driver 80, and pulls the suture thread 30 until the occluder is resting on the vessel 29 with the applicator 74 extending upwardly. Then, as shown in FIG. 8, the suture thread 30 is passed into the v-lock 36 of the wing 26 and under one of the hooks 78. In FIG. 9, the surgeon pulls on the suture thread 30 (arrow 82) while maintaining a firm yet delicate grip on the applicator 74/occluder 20 (arrow 84), until the desired compression and thus occlusion is achieved. The suture thread may be wrapped around the v-lock 36 several times if desired, as depicted in FIG. 1A. As may be seen in FIGS. 8, 9, the hooks 78 provide means for aiding in pulling the suture thread into the v-lock 36 by changing the direction of the pulling force from the less effective upward direction of arrow 82 to the more effective direction shown by arrow 85 in FIG. 9. In addition, the hook 78 concentrates the pulling force on the suture thread along the axis of the applicator 74 which reduces rotational and tilting forces and improves the control of the installation procedure.

At this stage, the suture thread is locked in the v-lock 36 and, as depicted in FIG. 10, the suture thread is clipped off near the occluder 20 with suitable scissors 87. Then the occluder 20 is held if necessary via forceps (not shown) to prevent rotation thereof while the applicator 74 is rotated (arrow 86) to unthread it from the bore 38 in the occluder 20. In accordance with the invention, all that remains on the heart surface is the installed low profile, unobtrusive occluder 20.

Figure 11:
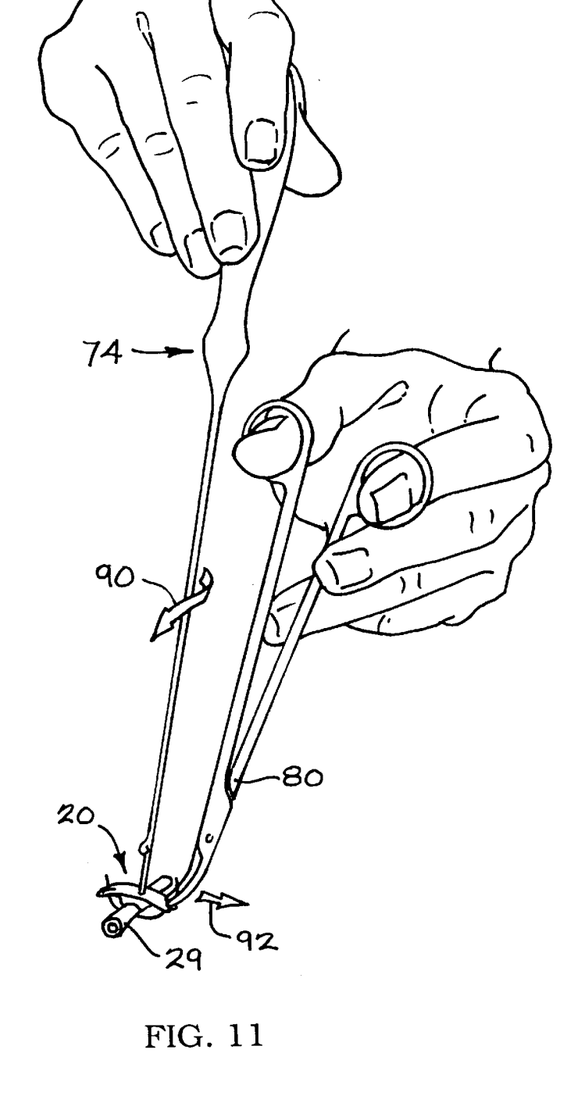
FIGS. 11 and 12 are perspective views illustrating several steps for removing an occluder of the invention from a vessel utilizing the applicator.
Figure 12:
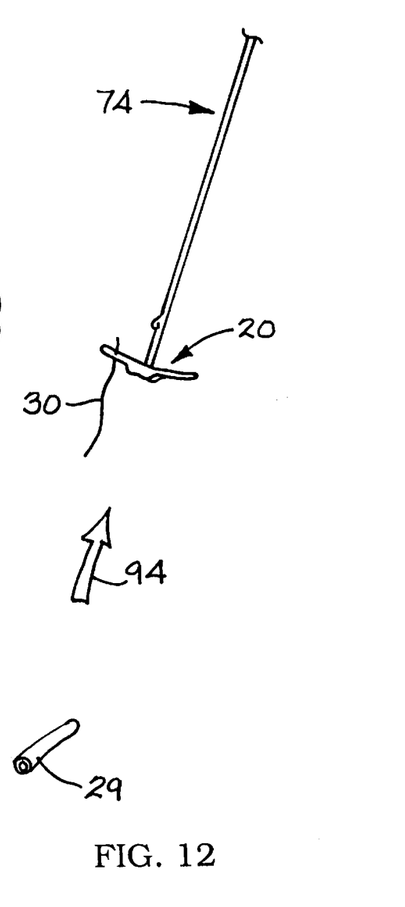

In FIGS. 11, 12, at such time as the CABG beating heart surgery is completed, or it is desirable to remove the occluder 20, 54 or 62, the surgeon inserts the threaded tip 42 into the threaded bore 38, holds the occluder 20 from rotation with the forceps/needle driver 80 if necessary, and rotates the applicator 74 (arrow 90) to thread the occluder onto the end of the applicator. The surgeon then grasps the end of the suture thread 30 above the v-lock 36 with forceps 80 and pulls sideways away from the occluder (arrow 92) to disengage the suture thread from the v-lock. The surgeon may also use the scissors 87 (FIG. 10) to cut the suture thread 30 just below the v-lock 36. The applicator 74 and attached occluder 20 then are lifted as a unit from the surgical opening as depicted by arrow 94 in FIG. 12, leaving the vessel 29 restored. During the removal, the suture thread slips out of the myocardial tissue.

Figure 13:
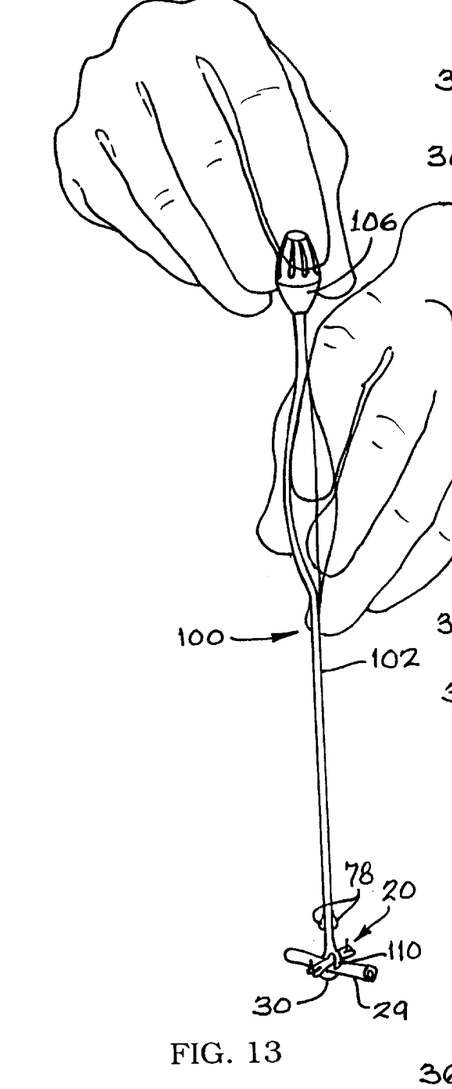
FIG. 13 is a perspective view illustrating an alternative embodiment of the applicator of the present invention.
Figure 14:
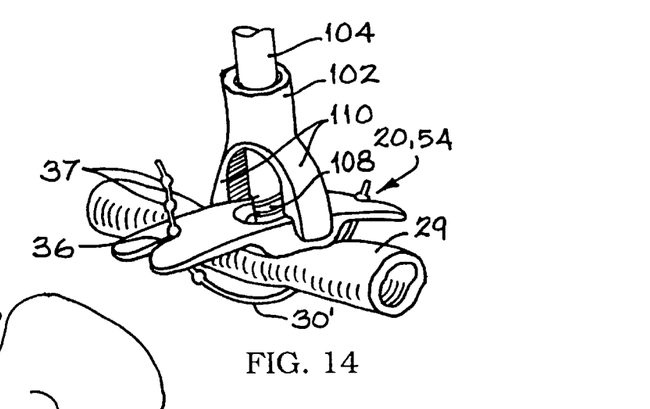
FIGS. 14, 15 and 16 are perspective views of the distal end of the invention of FIG. 13 illustrating means for preventing rotation of the occluder relative to a vessel during installation and removal.
Figure 15:
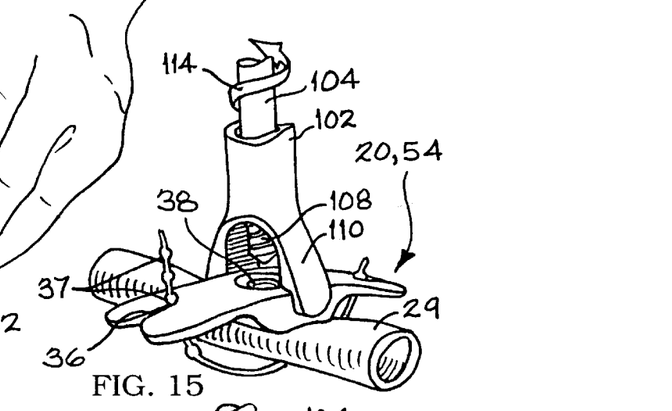
Figure 16:
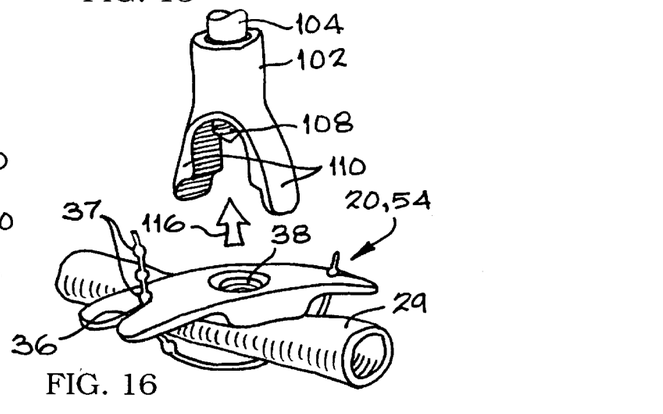

FIGS. 13–16 illustrate an alternative embodiment of an applicator 100 in accordance with the invention, which is modified with an anti-rotation handle 102 which replaces the handle 76 illustrated in FIGS. 6–12. Handle 102 is hollow along its full length to define a lumen therein. A rod 104 extends within the lumen the length of the handle 102, and is provided with a knob 106 at its proximal end (FIG. 13) and an externally threaded tip 108 at its distal end (FIGS. 14–16). Tip 108 may be similar to the tip 42 of previous description in FIGS. 2A, 2B.

As illustrated in FIG. 13, handle 102 is held stationary in position with one hand while the rod 104 is rotated and/or translated within the handle via the knob 106 with another hand. The distal end of the handle 102 is provided with an integral U-shaped grip, or holder 110, formed of fingers which are spaced apart an inside distance equal to the width of the occluder 20, 54, 62. Thus, as illustrated in FIGS. 14–16, when installing an occluder the handle 102/holder 110 is used to hold the occluder from rotating while the occluder is placed against the vessel 29, and the suture thread is passed under the vessel and locked into the v-lock 36, as previously described. The hook or hooks 78 are included above the distal end of the handle 102 and provide the same function.

The suture thread 30 in the embodiments of FIGS. 14–16 is modified as previously shown in FIG. 1B to include pre-formed "knots" or "bumps" 37 which insure that the suture thread will not slip from within the v-lock 36, thereby securing the occlusion. The bumps 37 preferably are oval or spherical in shape with no sharp edges to allow smooth and atraumatic passage through tissue surrounding the vessel 29. In practice, the occluder and knotted suture thread may be pre-formed, with one end of the suture thread molded or otherwise fixed to the wing 24 (or 66) as described previously. Because the "bumps" provide discrete suture positions, this suture thread configuration does not provide a continuous gradient of compression forces. Thus, it is preferable to make the distance between adjacent bumps as small as practical so that the compression force gradient is essentially continuous.

Once the occluder is installed, it is held from rotation by the holder 110 and anti-rotation handle 102, while the rod 104 is rotated as depicted by arrow 114 in FIG. 15, to unthread the tip 108 from the bore 38. Then, as depicted in FIG. 16, the combination handle 102 and rod 104 are removed from the occluder 20, 54, 62 (arrow 116) and the surgical opening (not shown). Only the low profile, unobtrusive occluder of the invention remains on the heart surface.

Although the occluders and associated applicators of the FIGS. 1–16 are described herein with specific elements, configurations and compositions by way of illustration, it is to be understood that various modifications will be evident to those skilled in the art without departing from the spirit and scope of the invention. To illustrate, the occluder may be formed of various materials such as, for example, spring steel or stainless steel ribbons with foam, soft plastic, etc., material molded thereto, or of plastics or polymers, etc. The suture thread 30 may be fluffy or smooth and formed of Gortex, nylon, etc., as is well known. Likewise, the applicators 74, 100 may be formed of suitable plastics in a disposable form, or of stainless steel, etc., if non-disposable.

Thus, the scope of the invention is defined by the following claims and their equivalents.

What is claimed is:

1. Apparatus including an occluder for occluding a blood vessel comprising:

a main member terminating in opposite ends and having a surface for atraumatic contact with the vessel;

a flexible member integral with and extending from a first end of the main member; and a suture thread secured to the flexible member and encompassing the vessel to secure to a second end of the main member under selected tension from the flexible member.

2. The apparatus of claim 1 including:

applicator means of predetermined length; and means for detachably securing the applicator means to the occluder, said applicator means enabling the installment of the occluder on the vessel while the applicator is attached to the occluder.

3. The apparatus of claim 2 wherein the means for detachably securing includes:

a threaded tip integral with a distal end of the applicator means; and a threaded bore, matching the threaded tip, formed in the main member.

4. The apparatus of claim 2 wherein the applicator means includes:
   a handle;
   a rod coaxially secured at its proximal end to the handle, with the means for detachably securing formed in a distal end of the rod.

5. The apparatus of claim 4 wherein the means for detachably securing includes:
   a threaded tip formed in the distal end of the rod; and
   a threaded bore formed in the main member for threadably engaging the threaded tip.

6. The apparatus of claim 2 wherein the applicator means includes:
   a handle having distal and proximal ends and a lumen extending therebetween; and
   a rod rotatably and translatably supported within the lumen with the means for detachably securing formed in a distal end of the rod.

7. The apparatus of claim 6 wherein:
   said handle includes holder means at its distal end for detachably holding the occluder; and
   the means for detachably securing includes a threaded tip formed on the distal end thereof, and a threaded bore in the main member for threadably engaging the threaded tip.

8. The apparatus of claim 1 including:
   an end member integral with and extending from the second end of the main member; and
   suture thread locking means formed in the end member for detachably locking the suture thread therein.

9. The apparatus of claim 8 wherein:
   the end member includes a second flexible member integral with and extending from the second end of the main member; and
   the suture thread locking means includes a v-lock formed in the second flexible member for detachably locking the suture thread therein.

10. The apparatus of claim 8 wherein:
    the suture thread locking means includes a vertical split having alternate meshing ridges and grooves formed therein for allowing sideways insertion of the suture thread while preventing vertical movement thereof.

11. The apparatus of claim 8 wherein:
    the main member includes a block shaped structure extending downwardly from the flexible member and the end member towards the vessel, with the atraumatic contact surface being formed on the vessel contacting surface of the block-like structure.

12. The apparatus of claim 1 wherein the suture thread includes preformed bumps spaced at intervals along a length thereof.

13. A method of occluding a blood vessel comprising the steps of:
    providing a vessel occluder having surface for atraumatic contact with the vessel, a flexible member, and a suture thread having a first end secured to said flexible member and a second free end;
    positioning said surface adjacent to said vessel;
    routine said second free end of said suture such that said vessel is positioned between said surface and a portion of said suture thread;
    pulling the suture thread with sufficient tension to cause the vessel to be occluded between said surface and said suture thread, said flexible member deforming in relation to said tension applied to the suture thread; and
    locking the suture thread to the vessel occluder whereby the deformed flexible member continues to supply tension to the suture thread to maintain a continuous compression and corresponding occlusion on the vessel.

14. The method of claim 13 including the steps of:
    attaching the vessel occluder to an applicator means to enable the steps of encompassing, applying and locking; and
    detaching the applicator means from the deformed flexible member after completion of the steps of positioning, routing, pulling and locking.

15. The method of claim 14 wherein the occlusion is to be removed, comprising the steps of:
    re-attaching the applicator means to the vessel occluder;
    unlocking the suture thread from the vessel occluder to release the tension maintained in the suture thread by the deformed flexible member; and
    withdrawing the vessel occluder and suture thread from about the vessel.

16. A method of occluding a blood vessel comprising the steps of:
    positioning a member against the vessel, said member including a flexible extension;
    affixing a first end of a suture thread to the member;
    threading a second end of the suture thread under the vessel to encompass the vessel within the member and the suture thread;
    applying tension on the suture thread to compress the vessel between the member and the suture thread; and
    securing the suture thread to the flexible extension to maintain the compression and thus occlusion of the vessel.

17. The method of claim 16 wherein the occlusion is to be removed, comprising the steps of:
    releasing the suture thread from the flexible extension to release the tension; and
    withdrawing the member and the suture thread from about the vessel to remove the occlusion.

18. The method of claim 16 including the steps of:
    securing an applicator means to the member to enable the steps of claim 18; and
    detaching the applicator means from the member upon completion of the steps of claim 18.

19. The method of claim 18 including the steps of:
    re-attaching the applicator means to the member;
    releasing the suture thread from the flexible extension to release the compression and occlusion on the vessel; and
    removing the member and suture thread from about the vessel.

20. An apparatus for occluding a blood vessel comprising:
    a main member having a first end, a second end, and a surface for atraumatic contact with the vessel;
    a flexible member extending outwardly from said main member;
    a suture thread having a first end secured to said flexible member and a second free end portion for encompassing said vessel; and
    said second end having an opening for receiving and securing said free end portion of said suture thread.

21. The apparatus of claim 20 further comprising an elongate applicator detachably connected to said vessel occluder.

22. The apparatus of claim 20 wherein said opening is a v-lock.

23. The apparatus of claim 20 wherein said opening comprises confronting surfaces having alternating ridges and grooves formed thereon.

24. The apparatus of claim 20 wherein said contacting surface is contoured.

25. The apparatus of claim 24 wherein said contacting surface is concave.

26. The apparatus of claim 24 wherein said contacting surface is convex.

* * * * *